United States Patent
Visconti

(10) Patent No.: US 9,888,845 B2
(45) Date of Patent: Feb. 13, 2018

(54) SYSTEM AND METHOD FOR OPTICAL DETECTION OF COGNITIVE IMPAIRMENT

(71) Applicant: Antonio Visconti, Menlo Park, CA (US)

(72) Inventor: Antonio Visconti, Menlo Park, CA (US)

(*) Notice: Subject to any disclaimer, the term of this patent is extended or adjusted under 35 U.S.C. 154(b) by 135 days.

(21) Appl. No.: 15/079,378

(22) Filed: Mar. 24, 2016

(65) Prior Publication Data

US 2017/0000344 A1 Jan. 5, 2017

Related U.S. Application Data

(60) Provisional application No. 62/187,042, filed on Jun. 30, 2015.

(51) Int. Cl.
| | |
|---|---|
| *A61B 3/14* | (2006.01) |
| *G06K 9/00* | (2006.01) |
| *A61B 5/16* | (2006.01) |
| *A61B 5/00* | (2006.01) |
| *G06K 9/20* | (2006.01) |
| *G06K 9/32* | (2006.01) |

(52) U.S. Cl.
CPC .......... *A61B 3/145* (2013.01); *A61B 5/16* (2013.01); *A61B 5/40* (2013.01); *A61B 5/4845* (2013.01); *A61B 5/7246* (2013.01); *G06K 9/0061* (2013.01); *G06K 9/00617* (2013.01); *G06K 9/2027* (2013.01); *G06K 9/3233* (2013.01)

(58) Field of Classification Search
CPC ....... A61B 5/1104; A61B 3/14; A61B 5/0077; A61B 5/026; A61B 5/04842; A61B 3/1241; A61B 5/14551; A61B 5/6821
USPC .............. 351/206, 218, 221, 223, 246, 205
See application file for complete search history.

(56) References Cited

U.S. PATENT DOCUMENTS

| | | |
|---|---|---|
| 4,850,961 A | 7/1989 | Gardner et al. |
| 5,422,690 A | 6/1995 | Rothberg et al. |
| 6,022,109 A | 2/2000 | Dal Santo |
| 7,338,166 B2 * | 3/2008 | Waldorf ............... A61B 3/112 351/205 |
| 2009/0115966 A1 | 5/2009 | Waldorf et al. |
| 2011/0058144 A1 | 3/2011 | Molnar et al. |
| 2014/0294245 A1 | 10/2014 | Siilats |

* cited by examiner

*Primary Examiner* — Hung Dang
(74) *Attorney, Agent, or Firm* — William Nuttle

(57) ABSTRACT

A system and method are provided for optical detection of cognitive impairment of a person using a portable video capture device (PVCD). In one embodiment, the method includes: (i) capturing video of an eye exposed to light stimuli over a predetermined time using a video camera of the PVCD; (ii) processing the video to locate at least one feature of the eye; (iii) measuring a change in the feature in response to the light stimuli; (iv) analyzing data from the measured change in the feature by extracting data from the measured change in the feature, calculating a number of parameters from the extracted data, correlating the calculated parameters with predetermined reference parameters and predicting a degree of impairment based on the results of the correlation; and (v) outputting through a user interface in the PVCD the degree of impairment to a user. Other embodiments are also described.

29 Claims, 15 Drawing Sheets

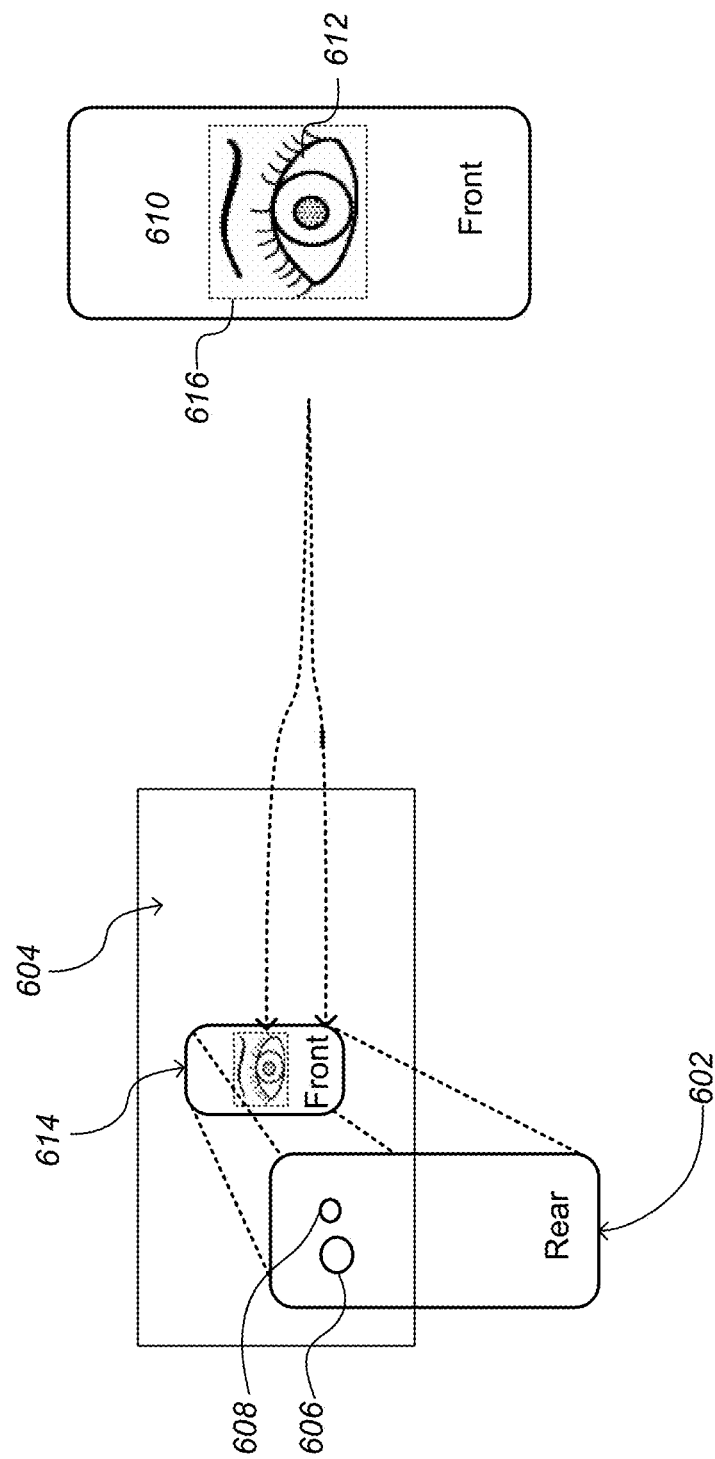

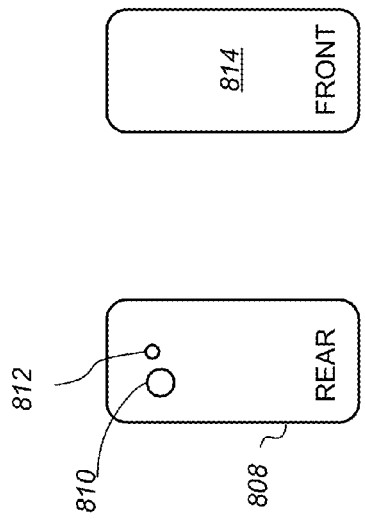
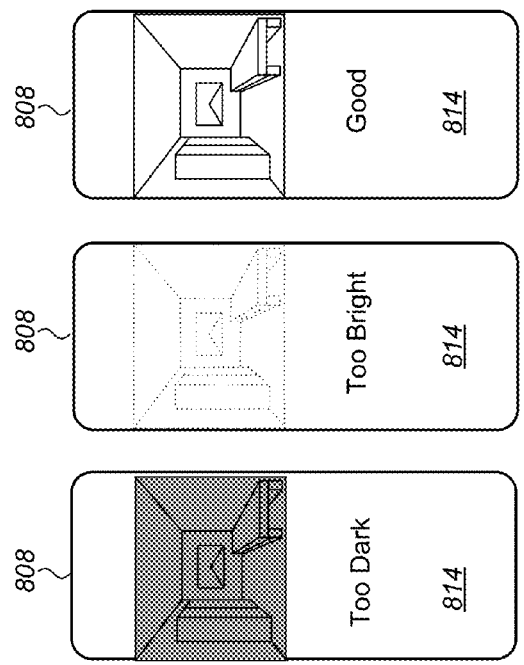
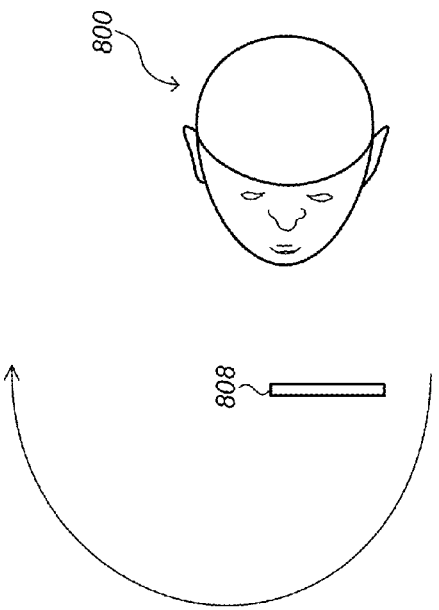
FIG. 8A
FIG. 8B
FIG. 8C

SYSTEM AND METHOD FOR OPTICAL DETECTION OF COGNITIVE IMPAIRMENT

CROSS-REFERENCE TO RELATED APPLICATIONS

This application claims the benefit of priority under 35 U.S.C. 119(e) to U.S. Provisional Patent Application Ser. No. 62/187,042, filed Jun. 30, 2015, which is incorporated by reference herein in its entirety.

TECHNICAL FIELD

The present disclosure relates generally to a system and method for optical detection of cognitive impairment, and more particularly to an application or software program designed to permit a user to optically detect cognitive impairment using a portable video capture device.

BACKGROUND

Cognitive impairment can be brought about by or the result of ingesting or otherwise introducing an intoxicating substance, such as alcohol or a drug, by an individual, or by a medical condition such as a concussion or fatigue. By cognitive impairment it is meant a diminution of a speed or quality in mental and motor functions of the effected individual. Cognitive impairment can include or result in loss or diminishment in judgment, self-control, reasoning, memory, speech and/or coordination.

Extreme cognitive impairment is readily recognizable to others, and, generally, to the individual—although because judgment is impaired the individual may not recognize or acknowledge the impairment. More problematic are situations in which the individual is only mildly impaired and thus may not be aware of any impairment at all. For example, because of a multitude of factors that affect blood alcohol concentration, i.e., age, gender, rate of consumption, body mass, food consumption and alcohol intolerance common among some ethnic groups, it is very difficult for an individual to assess his or her own impairment. While earlier stages of alcohol impairment may be undetectable to the drinker and others, it is known even small amounts of alcohol affect one's ability to drive, and a person will likely be too impaired to drive before appearing or maybe even feeling "drunk."

The same situation can arise when a person has suffered a blow to the head and have a concussion or is suffering from extreme fatigue, but insist that they 'feel fine,' and do not require medical attention or rest.

Thus, there is a need for an easy to use, portable and ubiquitous system and method to permit a person to quickly and accurately detect cognitive impairment in themselves and others.

SUMMARY

The objective of the invention is to provide a non-invasive, portable way to measure pupillary light reflex and other involuntary eye movements and correlate such measurement to an impairment level that can be associated with fatigue, alcohol, drug consumption or trauma. An important aspect of the invention is the implementation of it on a Portable Video Capture Devices like a Smartphone, a Personal Digital Assistants or a Tablet Computer that are carried by users on a regular basis for communication, entertainment, business or any other purpose.

Having the system implemented in such way significantly increase its use and benefits. Users do not have to plan to carry a dedicated instrument like a breath analyzer or a pupillometer to assess theirs or others level of impairment or relay only on individual judgment to make such assessment.

Another important aspect of the invention is the implementation of a Smart User Interface that will collect additional information by interacting with the user. The information collected includes physical characteristics like weight, height, sex, ethnicity, etc. as well specific information regarding the type of activities performed and the product consumed at the time preceding the test. The data is saved in a local database on the device and/or remotely to a server location and processed to construct a Reference Data Set by a Correlation and Prediction Process that will subsequently use the reference data set to extrapolate, at test time, an impairment level and a time to recovery. Depending on the kind of impairment, the Correlation and Prediction Process will correlate the Pupil Reflex to other impairment measurements. For example, in case of impairment due to alcohol consumption, a Blood Alcohol Concentration (BAC) value may be estimated.

Upon establishment that the subject under test may be impaired the SUI will be able to connect to network enabled transportation and/or emergency services, providing location data and other information for pick up and/or assistance of the impaired subject.

Furthermore, the invention may be used in public transportation environments, where for safety and liability reasons, a driver starting a working shift is required to self-test and submit the result to an employer to receive authorization to start driving. In such environment a positive identification of the subject under test is required and achieved via a bio metric measurement by applying an Iris Recognition algorithm to the same video captured with PVCD used for establishing impairment.

BRIEF DESCRIPTION OF THE DRAWINGS

Embodiments of the present invention will be understood more fully from the detailed description that follows and from the accompanying drawings and the appended claims provided below, where:

FIGS. 6A and 6B illustrate in greater detail a method to perform video capture using a PVCD having a rear facing camera and light source according to an embodiment of the present disclosure;

FIGS. 8A through 8C illustrate methods for using a light meter module to improve video capture according to embodiments of the present disclosure;

DETAILED DESCRIPTION

The present disclosure is directed generally to a system and method for testing for cognitive impairment due to the influence of alcohol, drugs, an injury or fatigue. Additionally, the invention may also be utilized to detect early sign of potential neurological damage following a trauma event like a concussion. In one embodiment, the system and method uses a free-hand portable testing apparatus to detect involuntary eye movement or reflex that are affected by fatigue, the consumption of alcohol, drugs, or trauma, and to inform users of the impairment level and an estimated recovery time before they may decide to operate, or not, a moving vehicle and decide or not to contact a transportation or emergency service or a trusted personal contact. Said involuntary eye movements can include pupil size changes due to light stimuli called Pupillary Light Reflex and small, jerk-like, involuntary eye movements called microsaccades.

In the following description, for purposes of explanation, numerous specific details are set forth in order to provide a thorough understanding of the present invention. It will be evident, however, to one skilled in the art that the present invention may be practiced without these specific details. In other instances, well-known structures, and techniques are not shown in detail or are shown in block diagram form in order to avoid unnecessarily obscuring an understanding of this description.

Reference in the description to "one embodiment" or "an embodiment" means that a particular feature, structure, or characteristic described in connection with the embodiment is included in at least one embodiment of the invention. The appearances of the phrase "in one embodiment" in various places in the specification do not necessarily all refer to the same embodiment. The term to couple as used herein may include both to directly electrically connect two or more components or elements and to indirectly connect through one or more intervening components.

Figure 1:
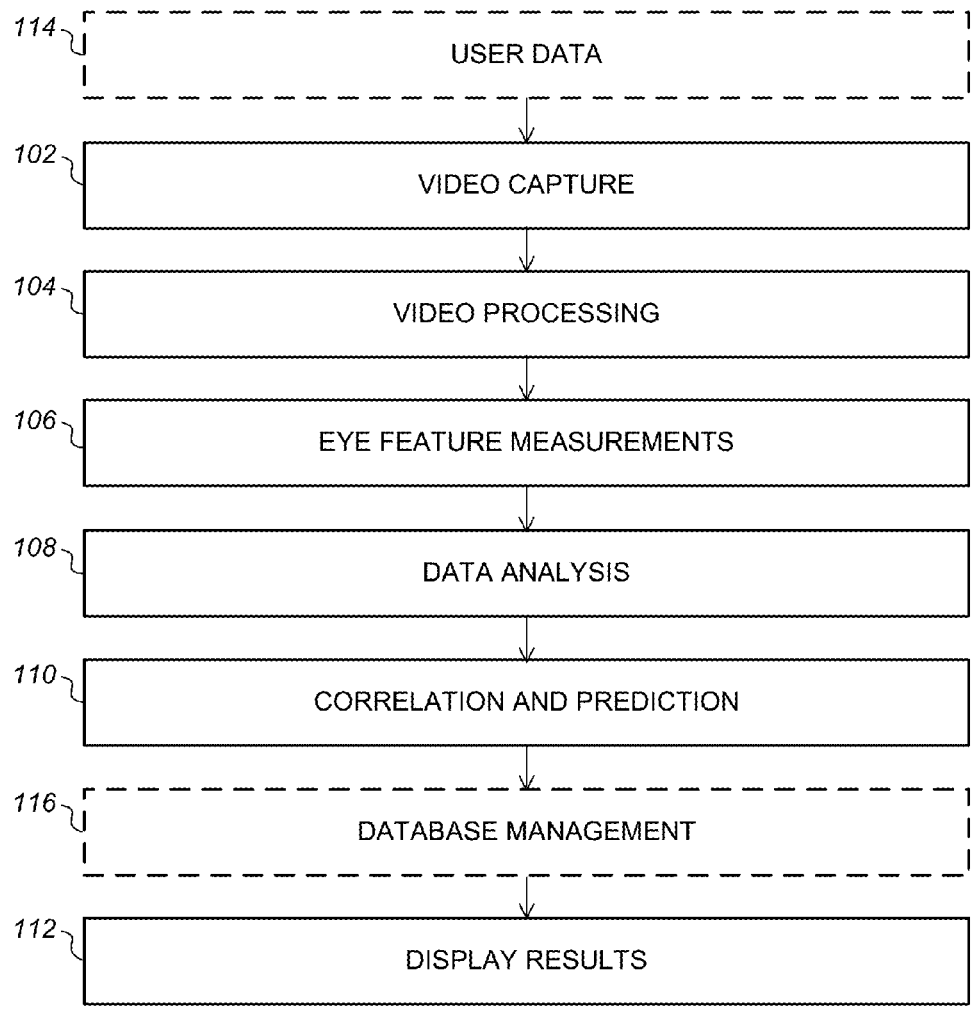
FIG. 1 is a flowchart illustrating a method to perform a cognitive impairment test according to an embodiment of the present disclosure.

FIG. 1 is a flowchart illustrating the most general embodiment of a method to perform a cognitive impairment test of a person according to an embodiment of the present disclosure. Each of the steps or block illustrated in FIG. 1 will be described in greater detail below with reference to FIGS. 2 through 13.

Referring to FIG. 1, the method begins with capturing video of an eye exposed to light stimuli over a predetermined time using a video camera of a portable video capture device or PVCD (102). Next, the captured video is processed to locate a feature of the eye (104). Features of the eye can include a pupil, an iris and/or a border between the pupil and the iris or any other discernible feature. A change in the located feature in response to the light stimuli over the predetermined time is measured (106). Next, data extracted from the measured change in the feature is analyzed (108). The data analysis can include calculating a number of parameters from the extracted data. Next, the calculated parameters are correlated with predetermined reference parameters in a database and a probability and degree of impairment predicted based on the results of the correlation (110). Finally, the resultant probability and degree of impairment of the person, is output through a user interface in the PVCD, such as a display and/or auditory interface to a user (112). It is noted that user may be the person undergoing the cognitive impairment test or another individual.

Optionally, as shown in FIG. 1, the method may further include an initial step of receiving from the user data on the person undergoing the cognitive impairment test (114), and updating or managing the database (116) with the resultant probability and degree of impairment of the person following the correlation and prediction step (110). User data can include a name of the person undergoing the cognitive impairment test, contact information, age, gender, height, weight, body mass, ethnicity, and other information required for the correlation and prediction step. The database may include a local database stored in a local memory of the PVCD, and/or a remote database stored in a remote memory coupled through a network to a network enabled PVCD.

Figure 2:
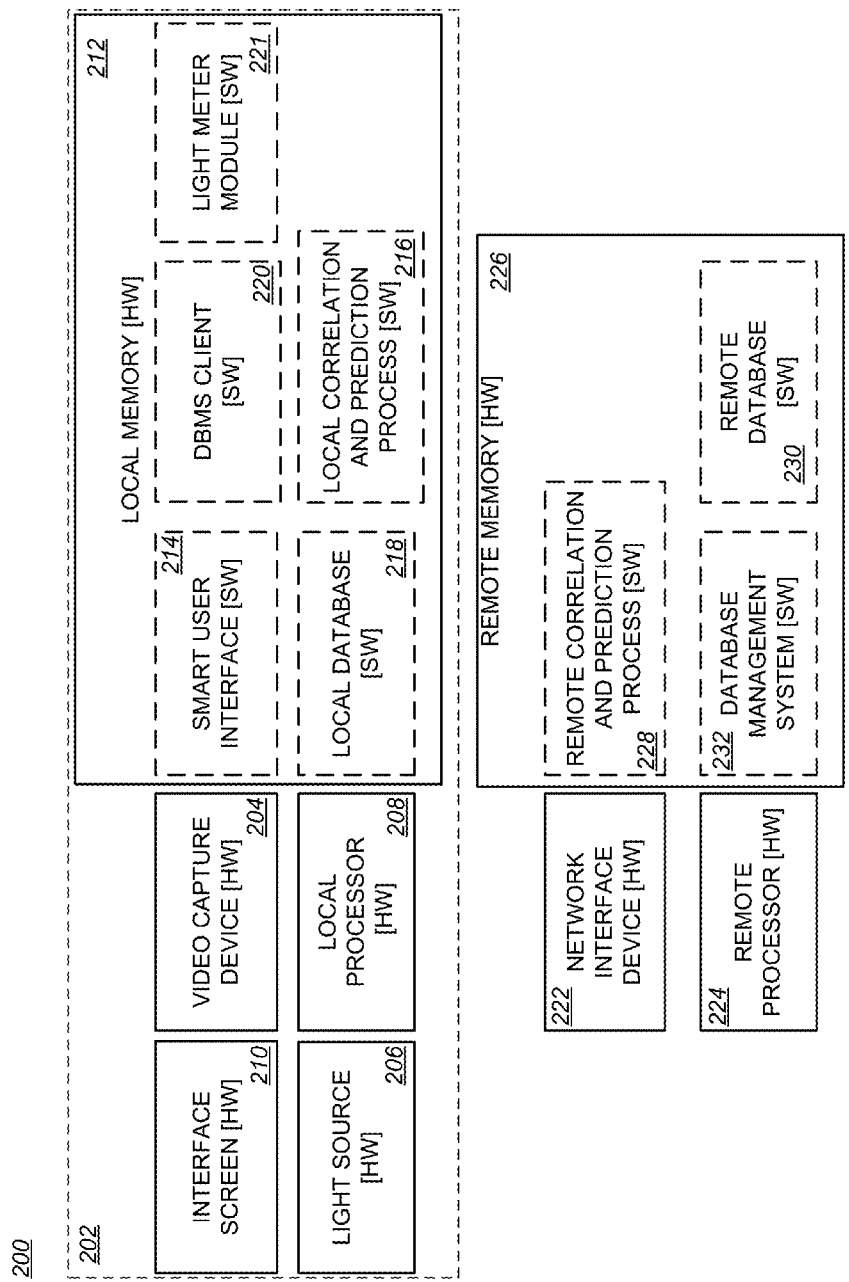
FIG. 2 illustrates a block diagram of a system according to an embodiment of the present disclosure.
Figure 3:
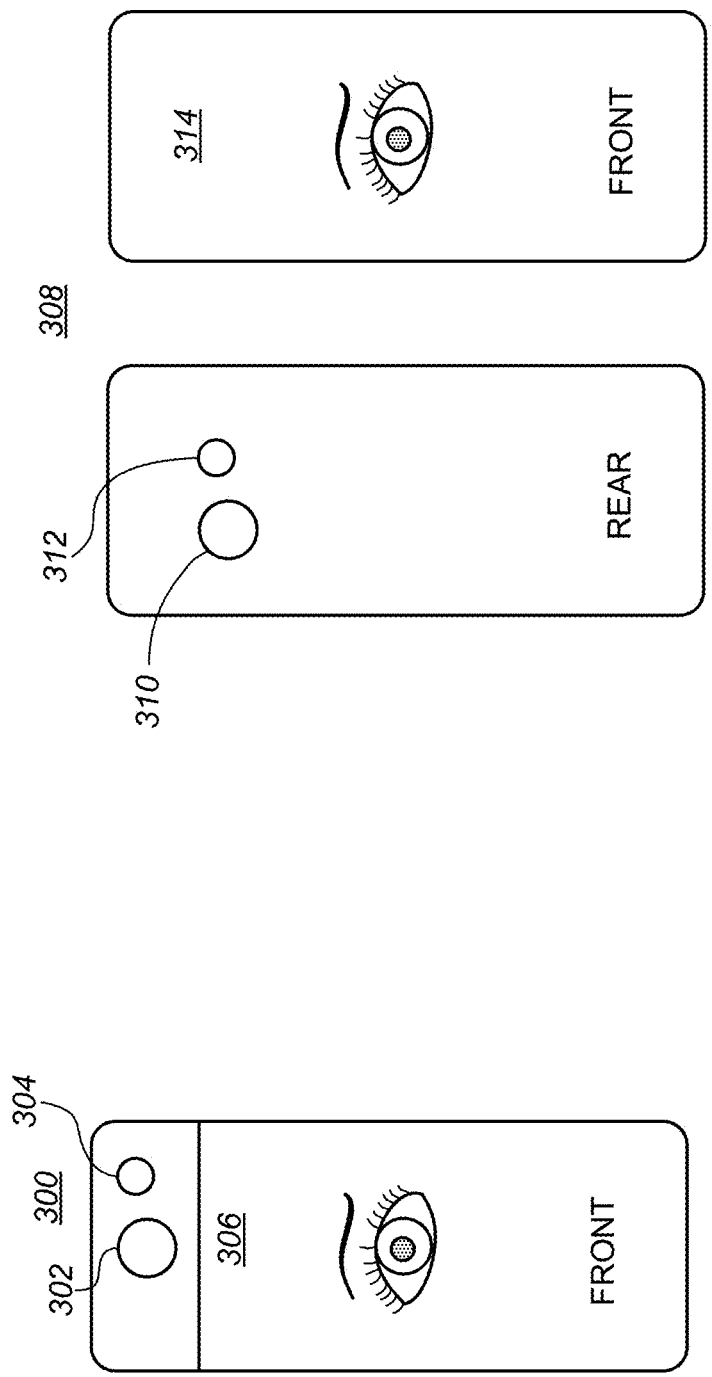
FIGS. 3A and 3B illustrate Portable Video Capturing Devices (PVCDs) suitable for use with the system and method of the present disclosure.

FIG. 2 illustrates a block diagram of a system 200 for performing a cognitive impairment test according to an embodiment of the present disclosure. Referring to FIG. 2 the system 200 generally includes a PVCD 202 having a video camera or video capture device 204, a light source 206, a local processor 208, a hardware interface 210, and a local memory 212. The video capture device 204 is configured or adapted to capture video over a predetermined time of an eye exposed to light stimuli generated by the light source 206. The local processor 208 is configured or adapted to execute a software program or application to locate and measure a change in a feature of the eye over the predetermined time, analyzing the changes and extracting data therefrom, calculating a number of parameters from the extracted data, and correlating the calculated parameters with predetermined reference parameters to predict a probability and degree of impairment. The hardware interface 210 can include a display and/or auditory device, to communicate to a user the probability and degree of impairment.

The local memory 212 can store software (SW) including user interface SW 214, local correlation and prediction process SW 216, a local database 218, database management system (DBMS) client SW 220 and light meter module (LMM) 221. The user interface SW 214 includes computer program code to communicate with the user via the hardware interface. The local correlation and prediction process SW 216 includes computer program code executed by the processor to locate and measure a change in a feature of the eye, analyze and extract data from the changes, and calculate and correlate a number of parameters with predetermined reference parameters to predict a probability and degree of impairment. The local database 218 includes computer program code to store and retrieve information necessary to perform the cognitive impairment test, including predetermined reference parameters and, optionally user data on the person undergoing test. The DBMS client SW 220 includes computer program code to update or managing the local database 218 with customized parameters used by the correlation and prediction process to calculate the resultant probability and degree of impairment of the person following the correlation and prediction step and store and maintain historical measurement data. The light meter module 221 includes computer program code to direct the user to reduce the impact of environmental or ambient light improving the video capture.

Optionally or preferably in some embodiments, such as that shown, the PVCD is a network enabled PVCD and the system 200 can further includes a network interface device 222, that connects to a cellular telephone tower or a wireless access point, through which the network enabled PVCD can be coupled to a remote processor 224 and/or a remote memory 226. Like the local processor 208, the remote processor 224 can be configured or adapted to execute one or more software programs including programs to locate and measure a change in a feature of the eye over the predetermined time, analyze the changes and extracting data therefrom, calculate a number of parameters from the extracted data, and correlate the calculated parameters with predetermined reference parameters to predict a probability and degree of impairment.

The remote memory 226 can store software (SW) including remote correlation and prediction process SW 228, a remote database 230, and database management system (DBMS) SW 232. The remote correlation and prediction process SW 228 includes computer program code executed by the processor to locate and measure a change in a feature of the eye, analyze and extract data from the changes, and calculate and correlate a number of parameters with predetermined reference parameters to predict a probability and degree of impairment. The remote database 230 includes computer program code to store and retrieve information necessary to perform the cognitive impairment test, including predetermined reference parameters and, optionally user data on the person undergoing test. The DBMS SW 230 includes computer program code to update or managing the remote database 230 with the resultant probability and degree of impairment of the person following the correlation and prediction step. It will be understood that the remote processor 224 and the remote database 232 can be desirably used to maintain and update data of all users of the system for the purpose of analyzing measurements and results over the large user base. The data is used for a continuous refinement of the correlation and prediction process.

Suitable PVCDs for use with the system and method of the present disclosure may include any portable, electronics device with video capture capability, a light source and a user interface, including, for example, a smartphone, a portable computer, personal digital assistant, a digital video camera, or a tablet computer. Preferably, the PVCD further includes a processor and is network enabled.

FIGS. 3A and 3B illustrate two different embodiments of smartphones suitable for use as PVCDs in the system and method of the present disclosure. Referring to FIG. 2A in the first embodiment the PVCD is a smartphone 300 having a front-facing video camera 302 and light source 304. By front-facing it is meant the video camera and light source are on the same side of the smartphone as a view-finder and interface screen or display 306. It will be understood that this arrangement or configuration is particularly advantageous when the user and the person undergoing cognitive testing are one and the same, i.e., for self-testing, as it simplifies the video capture process. Although, the system and method of the present disclosure are tolerant of movement during the predetermined time in which video is captured, generally the results are improved if the user can maintain the relative position of the eye to the camera throughout the predetermined time.

However, many current and previous generations of smartphones either do not include a front-facing video camera and light source, or a resolution of the front facing video camera is too low to work with the system and method of the present disclosure. Thus, in another embodiment, shown in FIG. 3B, the PVCD is a smartphone 308 having a rear-facing video camera 310 and light source 312. By rear-facing it is meant the video camera and light source are on the opposite side of the smartphone from the view-finder and interface screen or display 314. It will be understood that this arrangement or configuration is particularly advantageous when the user and the person undergoing cognitive testing are not the same, i.e., when a first person, the user, tests another, as it simplifies the video capture process. This embodiment is particularly advantageous when the suspected cognitive impairment is the result of fatigue or a medical condition, such as a concussion, which may make it difficult for a self-testing user to maintain the relative position of the eye to the camera throughout the predetermined time. It will further be understood, that this embodiment can still be used for self-testing by use of a mirror or reflecting surface, and/or a positioning device (not shown in this figure) removably attached to the smartphone, and/or with an embedded real time position detection processing providing audio feedback to user which will be described in greater detail below.

Suitable for PVCD with access to camera real time parameters like focus distance, lens position and other significant parameters and/or real time video processing capability. The distance of the PVCD from the user under test is estimated by analyzing in real time the retrieved camera parameters and/or video frames and provide visual and/or audible guidance to the user to adjust a distance between the eye and the camera of the PVCD.

Figure 4:
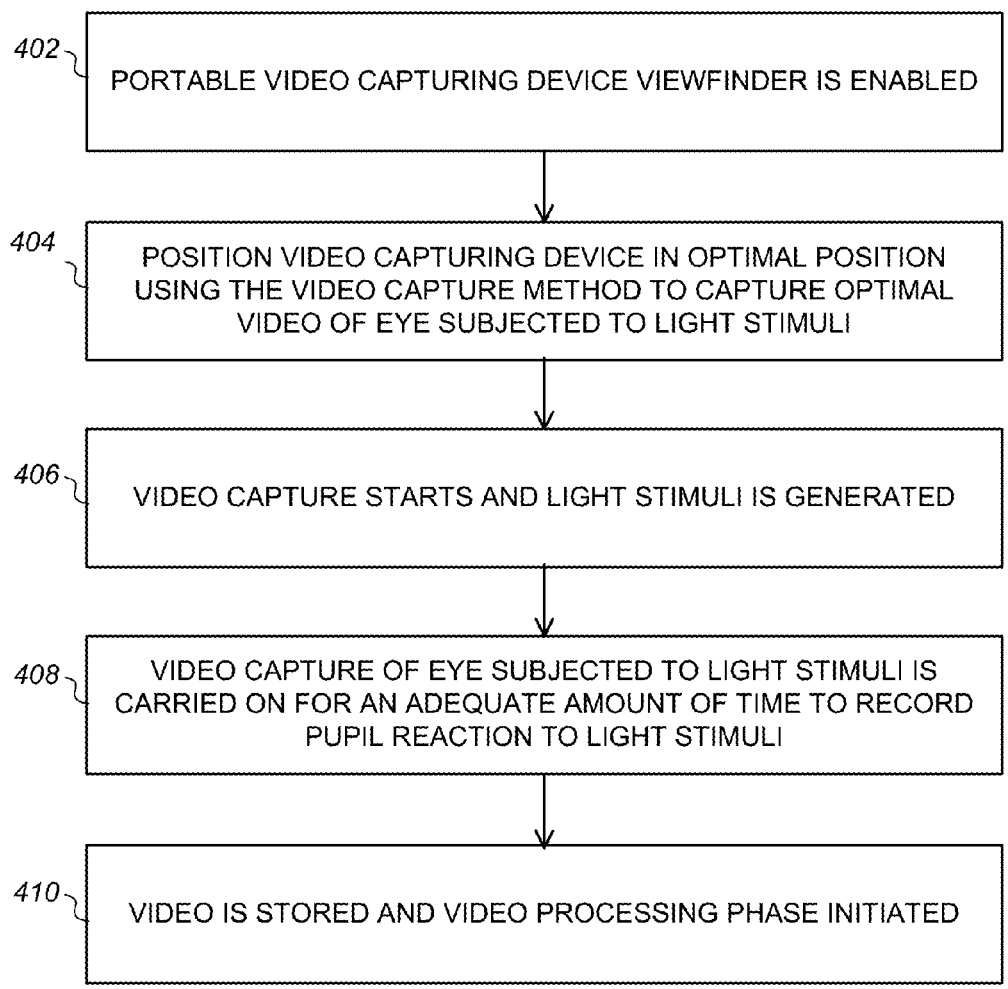
FIG. 4 is a flowchart illustrating a method to perform video capture according to an embodiment of the present disclosure.

Methods of performing video capture according to the system and method of the present disclosure will now be described with reference to FIGS. 4 through 6B. FIG. 4 is a flowchart illustrating a method to perform video capture according to one embodiment of the present disclosure. Referring to FIG. 4, the method begins with a user enabling a viewfinder of the PVCD (402). The user then positions the PVCD in an optimal position (described in greater detail below with reference to FIG. 7) to capture video of an eye of the person undergoing test and subjected to light stimuli (404). Next, video capture starts and a light stimulus is generated (406). Video capture of eye subjected to light stimuli is carried on for a predetermined amount of time to record pupil reaction to light stimuli (408). The video is then stored and video processing phase is initiated (410).

Figures 5A, 5B, 5C:
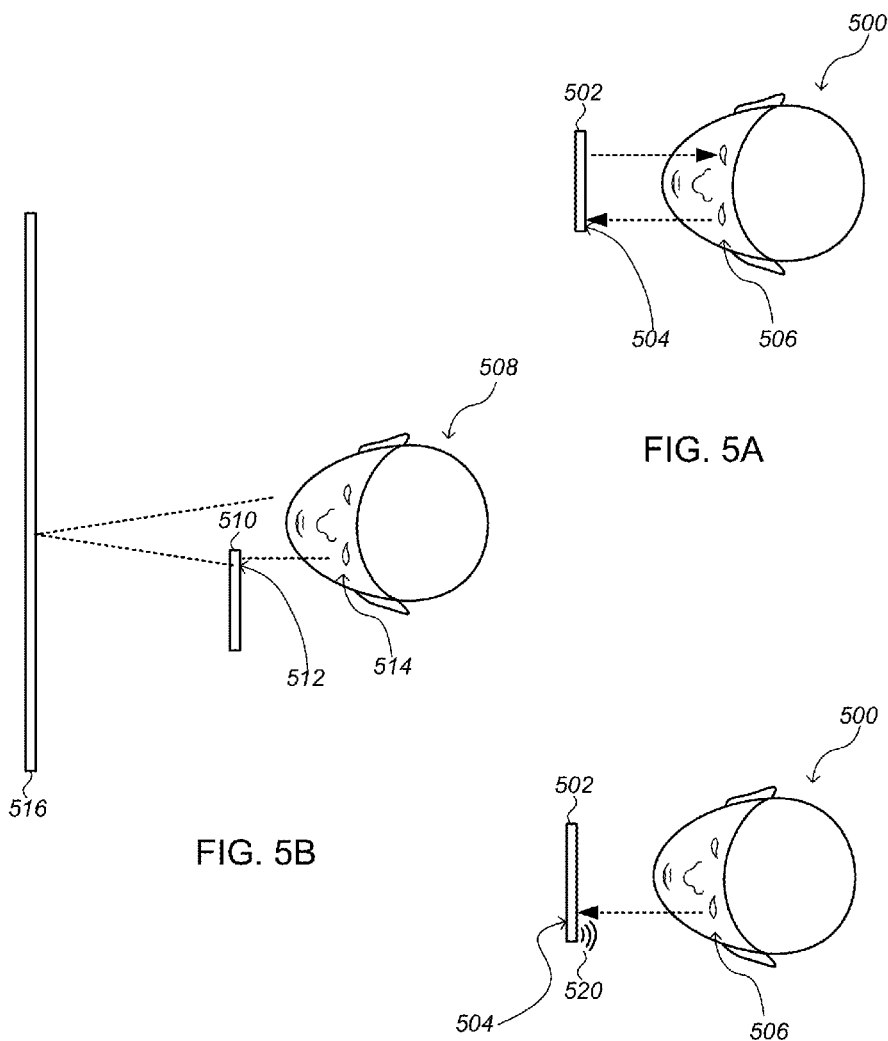
FIGS. 5A through 5C illustrate free-hand methods to perform video capture using different types of PVCDs according to embodiments of the present disclosure.

FIGS. 5A, 5B and 5C illustrate two free-hand methods to perform video capture using different types of PVCDs according to embodiments of the present disclosure.

FIG. 5A illustrates a free-hand method in which a user 500 and the person undergoing cognitive testing are one and the same, i.e., for self-testing, using a PVCD (smartphone 502) having a front-facing video camera and light source on the same side of the smartphone as a view-finder and interface screen or display 504. This configuration enables the user to maintain the relative position of an eye 506 to the camera throughout the predetermined time.

FIG. 5B illustrates another free-hand method in which the user 508 and the person undergoing cognitive testing are one and the same, i.e., for self-testing, using a PVCD (smartphone 510) having a rear-facing video camera and light source on the opposite side of the smartphone as a view-finder and interface screen or display 512. This configuration enables the user to maintain the relative position of an eye 514 to the camera throughout the predetermined time using a mirror 516.

FIG. 5C illustrate another free-hand method suitable for PVCD with real time access to camera parameters like focus distance, lens position and other significant parameters and/or real time video processing capability. This embodiment further uses an audible device, such as a speaker in the PVCD to produce an audible signal 520 to provide audible and/or visible guidance based on the reading of the camera parameters and/or data from real time processing of video frames. This configuration enables the user to maintain the relative position of an eye 506 to the camera throughout the predetermined time, without the use of mirror or viewfinder screen. This configuration can be used for PVCD with either rear or front facing camera and light source FIGS. 6A and 6B illustrate in greater detail a method for optimal self-capture video of own eye using a PVCD having a rear facing camera and light source, such as the embodiment of FIG. 5B above. Referring to FIGS. 6A and 6B, the method consists of a dedicated Smart User Interface software (SUI) running on the PVCD 602 and the use of a mirror 604 to guide a user to correctly a PVCD having a rear facing camera 606 and light source 608 to perform an optimal video capture operation. The user will position him or herself in front of the mirror 604 to interact with the viewfinder and input screen 610 while pointing the camera and light source to own eye 612 for video capture. The SUI will guide the user by providing positioning instruction in a mirrored fashion in order to make them appear normal in the mirror reflection 614. The SUI can also display a framing mask 616 to guide the user to position the PVCD at the optimal distance for video capture. The size and position of the eye as seen in the framing mask provides the necessary feedback to user for optimal positioning of PVCD. Optionally, the SUI can also provide instructions in an audible form, utilizing the sound capability of the smartphone PVCB.

Figure 7A:
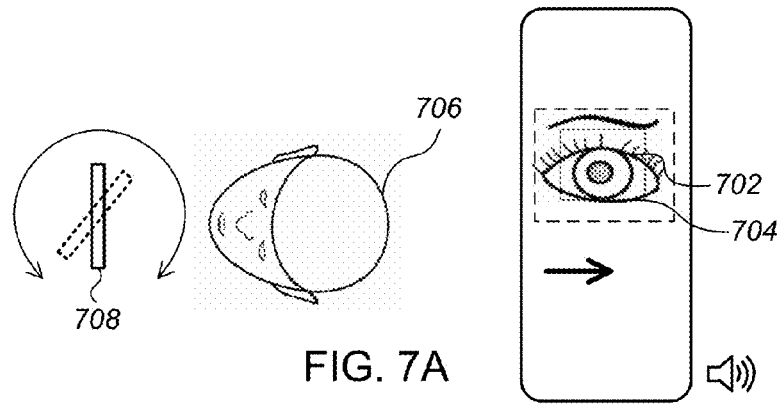
FIGS. 7A through 7C illustrate methods for providing feedback to improve accuracy in free-hand methods to perform video capture according to embodiments of the present disclosure.
Figure 7B:
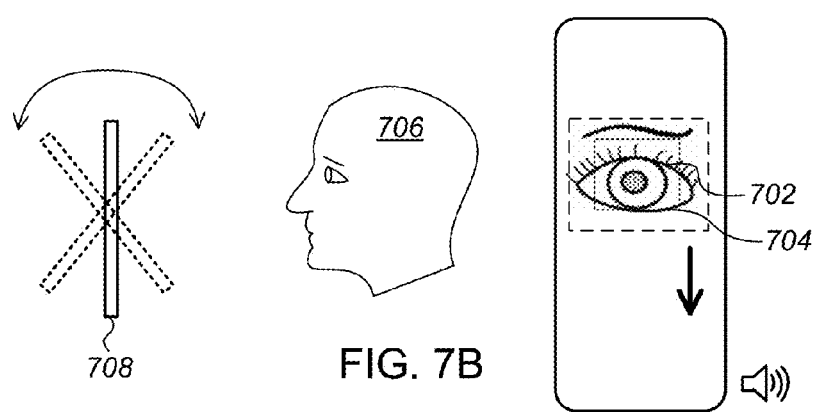
Figure 7C:
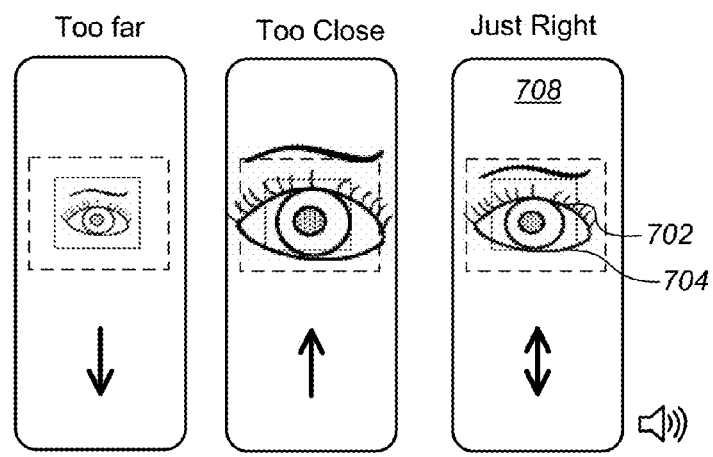

In either embodiment, i.e., a PVCD having rear facing camera or a front facing camera, the accuracy of the measurement is affected by the hand movements of the user holding the PVCD. FIGS. 7A through 7C illustrate in greater detail how the SUI can use PVCD sensors data from accelerometer, gyroscope, magnetometer and/or an image of the eye 702 in relation to framing mask 704 to guide in real time a user 706 to optimal positioning of the PVCD 708. In particular, FIG. 7A illustrates how the SUI can provide rotation feedback in visual and/or audible form. FIG. 7B illustrates how the SUI can provide tilt feedback in visual and/or audible form. And FIG. 7C illustrates how the SUI can provide distance feedback in visual and/or audible form.

FIGS. 8A through 8C illustrate methods for using the light meter module (LMM) to direct the user to reduce the impact of environmental or ambient light improving the video capture. Referring to FIG. 8A in one embodiment, the PVCD is a smartphone 808 having a rear-facing video camera 810 and light source 812. By rear-facing it is meant the video camera and light source are on the opposite side of the smartphone from the view-finder and interface screen or display 814. Referring to the left hand figure of FIG. 8B it is seen that the environmental or ambient light is too dark negatively impacting video capture. Similarly, the middle figure of FIG. 8B illustrates a condition in which the environmental or ambient light is too bright. FIG. 8C illustrates how the use may be prompted using either visual and/or audible signal from the PVCD to reposition him or herself relative to ambient light to provide a condition in which the environmental or ambient light provides a good video capture—illustrated in FIG. 8C.

Figure 9B:
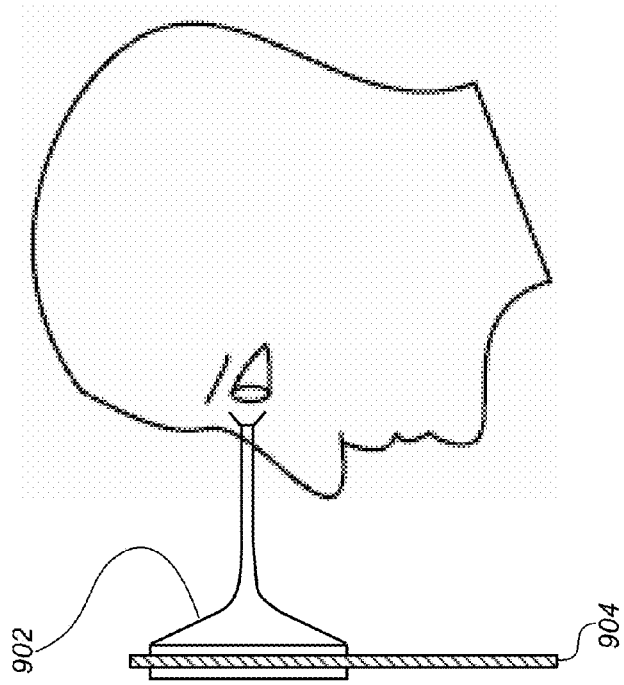
FIGS. 9A and 9B illustrate a method to perform video capture using an add-on positioning device with the PVCD according to another embodiment of the present disclosure.
Figure 9A:
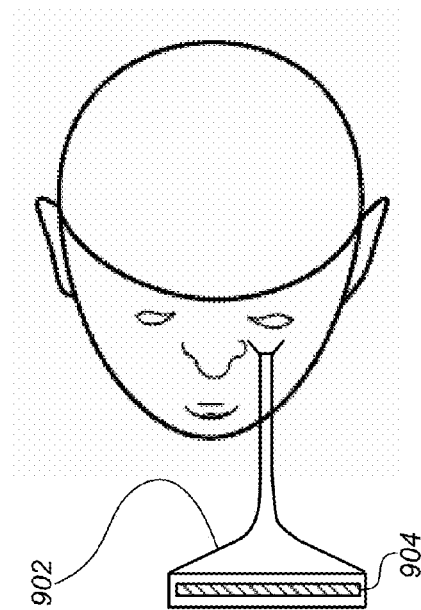
Figure 10:
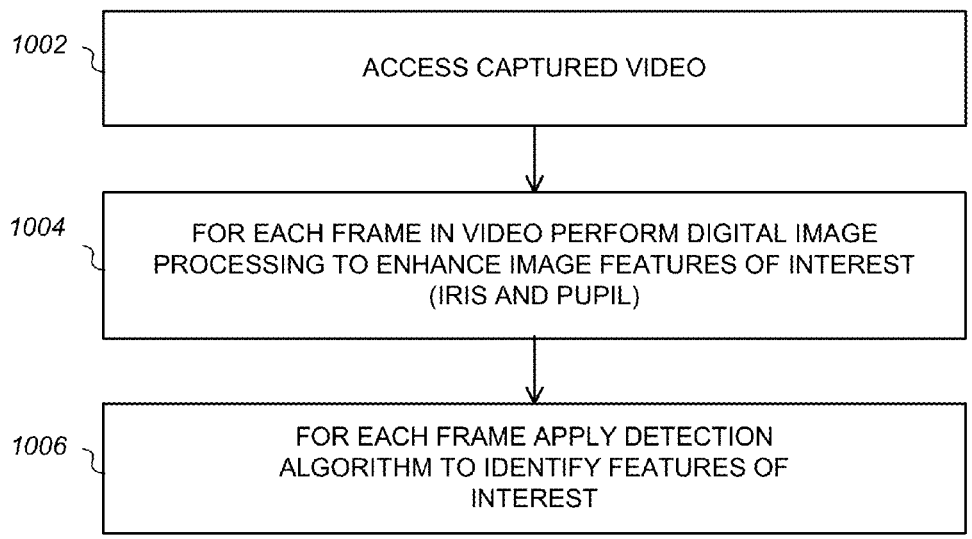
FIG. 10 is a flowchart illustrating a method to perform video processing according to an embodiment of the present disclosure.

FIGS. 9A and 9B illustrate an alternative method to position the PVCD in optimal position to perform video capture using an add-on positioning device 902 removably attached to a PVCD 904. It will be appreciated that this method can be used to perform video capture using either a PVCD having rear facing camera or a front facing camera FIG. 10 is a flowchart illustrating a method to perform video processing according to one embodiment of the present disclosure. Referring to FIG. 10, the method begins with a processor, either the local processor 208 in the PVCD or the remote processor 224, accessing captured video (1002). Typically, the captured video is stored in local memory 212; however it may alternatively be stored in remote memory 226. Next, for each frame in video digital image processing is performed using the processor to enhance image features of interest, such as the iris and pupil (1004). Finally, for each frame the processor applies a detection algorithm to identify the features of interest (1006), after which eye feature measurements are performed.

Figure 11:
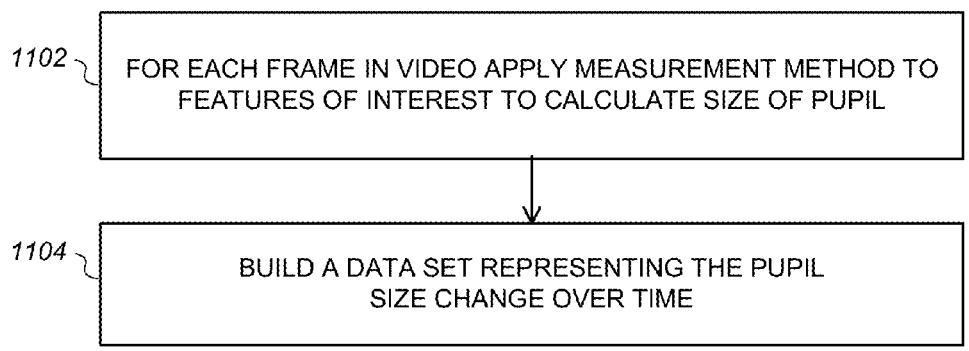
FIG. 11 is a flowchart illustrating a method to perform eye feature(s) measurements according to an embodiment of the present disclosure.

FIG. 11 is a flowchart illustrating a method to perform eye feature(s) measurements according to one embodiment of the present disclosure. Referring to FIG. 11, the method begins with the processor for each frame in the captured and processed video applying a measurement method to features of interest to calculate size of pupil for each frame (1102). Next, a data set is built representing a change in pupil size over time, such that videos captured at "n" frames per second, will provide "n" consecutive measurements representing the change in pupil size over a 1 second time period (1104).

The method consists of measuring in each frame of the captured video, both the size of the pupil and the iris and/or any other relevant image feature in the captured video that is not affected by the light stimuli, i.e., the iris. After features of interest identification, the size measurement is performed by the measurement algorithm and it may consist of counting the pixel in the image feature of interest, and/or fitting curves like circles or ellipses, or any other geometrical shape to the area and/or perimeter of the features of interest from which a size calculation is performed. After the measurements are performed a compensation algorithm will analyze the change of size of pupil and iris from frame to frame. Any change in size of iris is due to PVCD movement only, while changes in pupil size are due to both to pupil reaction to light stimuli and PVCD movements. The compensation algorithm will use the change in the size of iris to extrapolate the pupil size change due only to the light stimuli, effectively removing the effect of the PVCD movement from the pupil size measurement and provide an accurate measurement of pupil size change due to light stimuli only. The types of movements that affect the measurements are forward and backward motion, rotation around the vertical axis and tilt around the horizontal axis.

FIGS. 12A through 12D illustrate eye feature(s) measured, the effect of a light source on the eye feature(s), and methods to accurately measure change in pupil dimension in a video recording due to light stimuli while compensating measurement error due to movement of video capturing device.

Figure 12A:
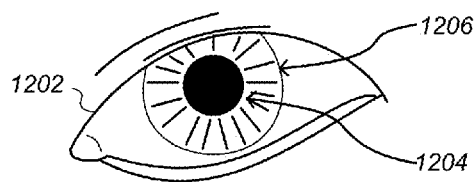
FIGS. 12A through 12D illustrate eye feature(s) measured, the effect of a light source on the eye feature(s), and the effect of PVCD movement on eye feature(s) captured according to embodiments of the present disclosure.
Figure 12B:
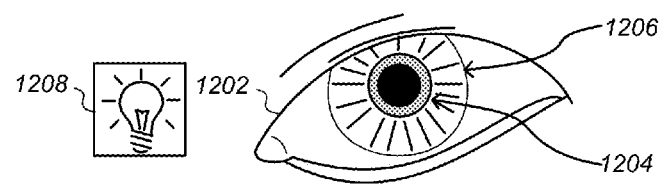

FIG. 12A shows an eye 1202 including a pupil 1204 and an iris 1206 prior to exposure to light stimuli. It is noted that the iris 1206, unlike the pupil 1204 is not affected by light. FIG. 12B shows an eye 1202 including a pupil 1204 and an iris 1206 after exposure to light stimuli from a light source 1208. It is noted that the pupil 1204 contracted.

Figure 12C:
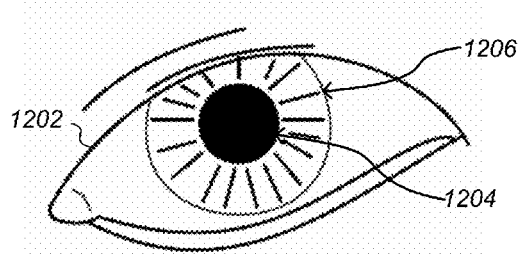
Figure 12D:
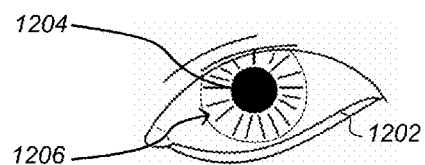

FIGS. 12C and 12D shows the effect of camera movement on pupil size and an iris 1206 in captured video frames. Referring to FIG. 12C it is noted as the camera (PVCD) moves closer to the eye both the pupil 1204 and iris 1206 get larger. FIG. 12D shows that as the camera (PVCD) moves away from the eye both the pupil 1204 and iris 1206 get smaller. Thus, in prior art approaches to measuring pupil contraction or dilation the camera was required to be fixed relative to the eye. In contrast, in the method using the system, which measures the pupil size relative to an outer edge of the iris, are therefore tolerant of movement during the predetermined time in which video is captured.

Figure 13A:
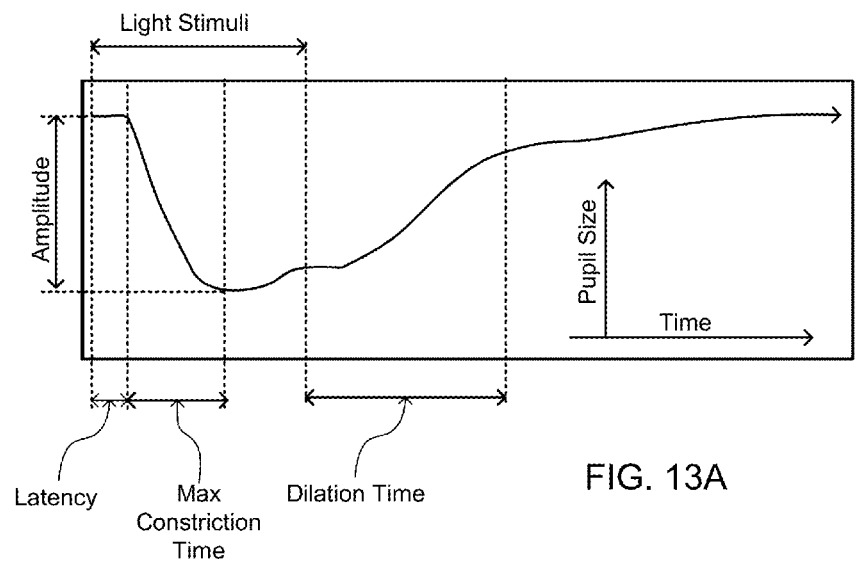
FIG. 13A is a graph of pupillary constriction measured according to embodiments of the present disclosure.
Figure 13B:
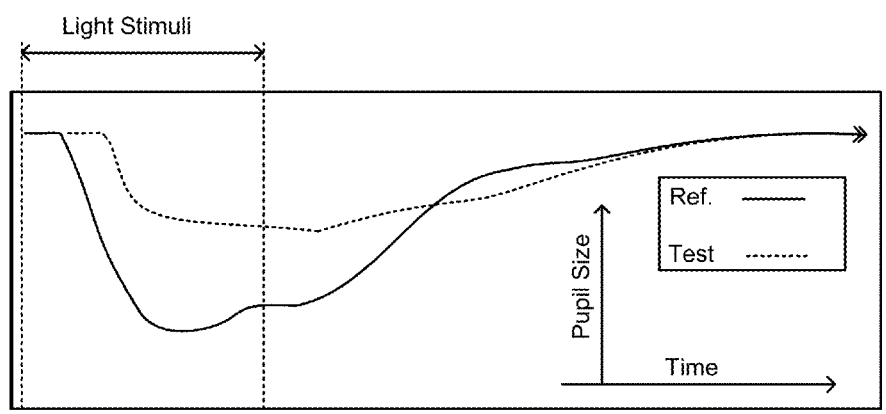
FIG. 13B is a graph of pupillary dilation following constriction measured according to embodiments of the present disclosure.

Data analysis is the process of extracting critical information from the eye features measurement process. The data analysis performed will now be described with reference to FIGS. 13A and 13B. FIG. 13A is a graph of pupillary constriction and FIG. 13B is a graph of pupillary dilation following constriction measured according to embodiments of the present disclosure.

Referring to FIG. 13A, a normal reaction to a high intensity light stimuli consist in pupillary constriction after a latency period. Referring to FIG. 13B, after constriction, pupillary re-dilation occurs and eventually the original, pre-stimulus size is reached again when the light stimuli is removed. Several parameters are calculated and stored, like amplitude, latency, max constriction time, dilation time, other parameters and variation of current test data against a Reference Data Set.

Figure 14:
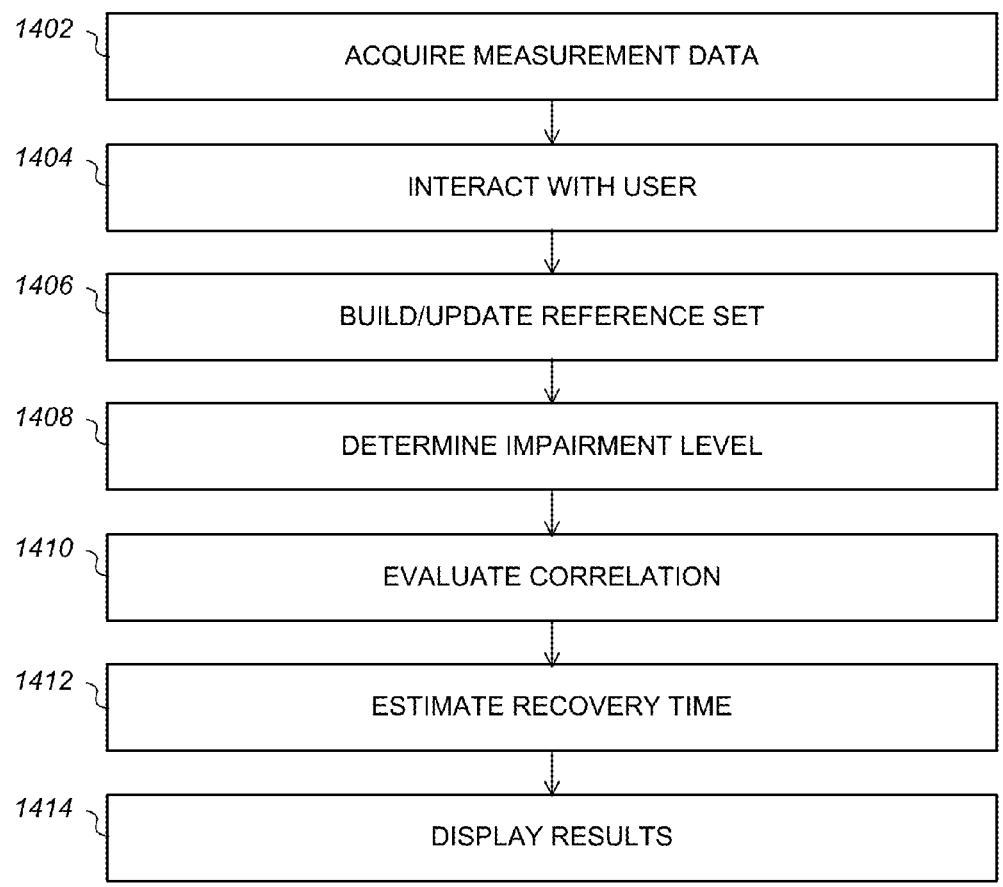
FIG. 14 is a flowchart illustrating a method to perform correlation and prediction process according to an embodiment of the present disclosure.

FIG. 14 is a flowchart illustrating a method to perform a correlation and prediction process according to one embodiment of the present disclosure. Referring to FIG. 14, the method begins with acquiring measurement data (1402). Next, the system interacts with user (1404). By interact with the user it is meant that the user interface may request additional information from the user, like activities performed before the test, if alcohol or any other substance has been consumed. This additional information is used to correlate the impairment level to other impairment measurements. For example, in case of impairment due to alcohol consumption, a Blood Alcohol Concentration (BAC) value may be estimated. A reference set including reference parameters is built and/or updated (1406). Next, the level of impairment of the person undergoing test is determined by comparing calculated parameters to the reference parameters (1408), a significant variation of pupil reflex is always an indication of some sort of impairment, subsequently with or without the additional information provided by the user, the correlation to other impairment measures is evaluated (1410). Where the impairment is due to intoxication, a recovery time can be estimated (1412) or for some other kind of impairment a recommendation of seeking immediate medical help can be provided. Finally, the results are displayed to a user (1414).

Figure 15:
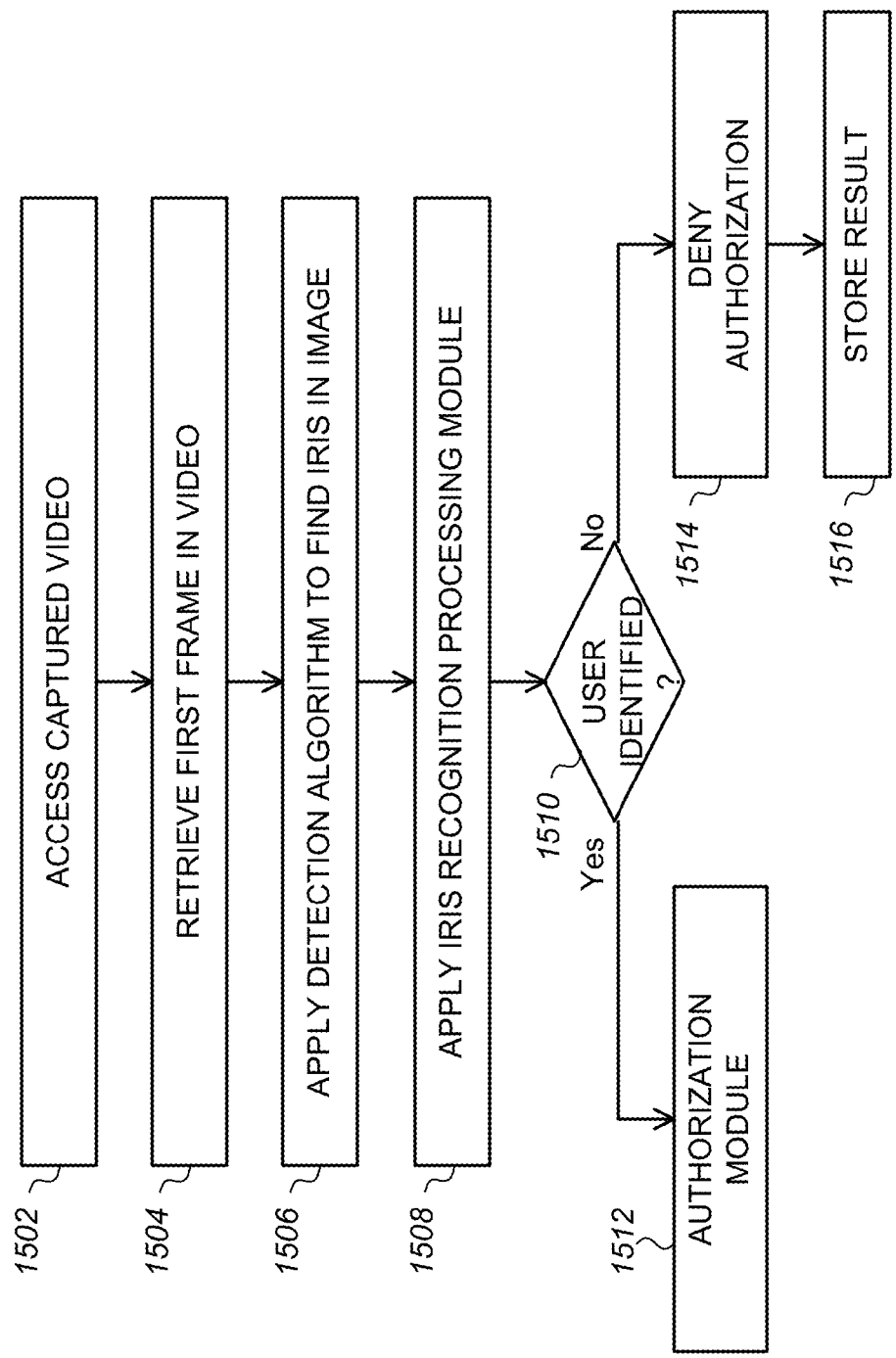
FIG. 15 is a flowchart illustrating a method to perform user identification according to an embodiment of the present disclosure.
Figure 16:
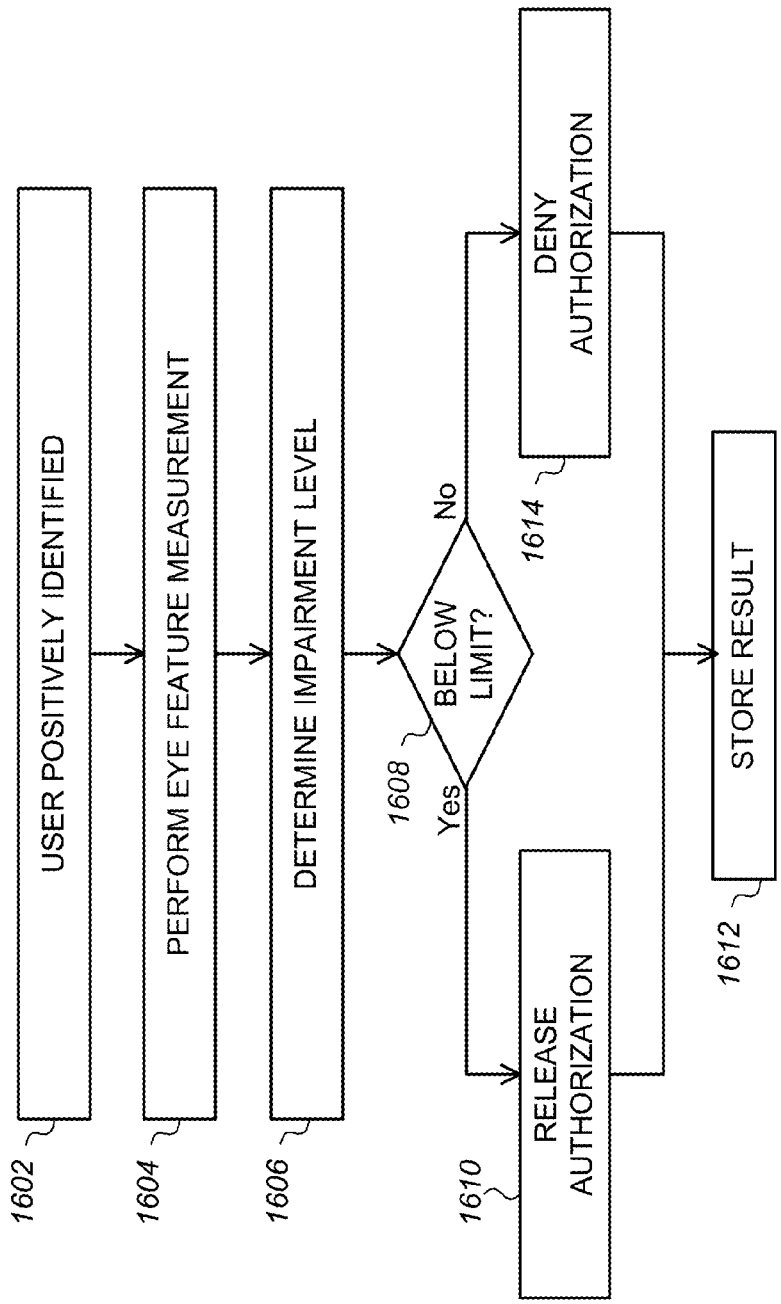
FIG. 16 is a flowchart illustrating a method to perform user authorization according to an embodiment of the present disclosure.

FIGS. 15 and 16 illustrate an alternative method further including software modules to perform user identification and authorization using captured image or video from the PVCD. In particular, FIG. 15 is a flowchart illustrating a method to perform user identification through iris recognition according to an embodiment of the present disclosure. FIG. 16 is a flowchart illustrating a method to perform user authorization according to an embodiment of the present disclosure. It will be understood that the user identification or iris recognition module, and the authorization module can be either in the local memory 212 or the remote memory 226 shown in FIG. 2.

Referring to FIG. 15, the process begins with user identification through iris recognition with access the captured video (1502) and retrieving the first frame in that video (1504). Next, the detection algorithm is applied to find an iris in the image of the first frame (1506). An iris recognition processing module is then used to compare the iris in the image of the first frame, to a stored image of the user. Once the user has been identified, i.e., the iris in the image of the first frame matches a stored image of the user (1510), the method proceeds to the authorization module (1512) to begin testing. If the iris in the image of the first frame does not match the stored image of the user, authorization is denied (1514), and the result, the failed authorization attempt is stored (1516).

Referring to FIG. 16, once the user has been positively identified (1602), the eye feature measurement is performed (1604) and an impairment level determined (1606). The eye feature measurement and determination of impairment level can be accomplished using the methods, processes and algorithms described above with reference to FIGS. 1, 4 and 14. Once the user identity has been confirmed, i.e., the iris in the video matches a stored image of the user (1608), the method proceeds to the release authorization (1610) and the results of the eye feature measurement and determination of impairment level are stored (1612). If the user identity has been confirmed, i.e., the iris in the video does not match the stored image of the user, authorization is denied (1614), and the result, the failed authorization attempt.

Optionally, where the PVCD is a network enabled device, such as a smartphone, the method can further include providing contact information or even automatically connect to network enabled transportation, emergency services, and/or to or a trusted personal contact previously given by the person undergoing test to render assistance.

Optionally where the invention may be used in public transportation environments, where for safety and liability reasons, a driver starting a working shift is required to self-test and submit the result to an employer to receive authorization to start driving.

Thus, embodiments of to a system and method for testing for cognitive impairment due to the influence of alcohol, drugs, an injury or fatigue have been described. Although the present disclosure has been described with reference to specific exemplary embodiments, it will be evident that various modifications and changes may be made to these embodiments without departing from the broader spirit and scope of the disclosure. Accordingly, the specification and drawings are to be regarded in an illustrative rather than a restrictive sense.

The Abstract of the Disclosure is provided to comply with 37 C.F.R. §1.72(b), requiring an abstract that will allow the reader to quickly ascertain the nature of one or more embodiments of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

Reference in the description to one embodiment or an embodiment means that a particular feature, structure, or characteristic described in connection with the embodiment is included in at least one embodiment of the circuit or method. The appearances of the phrase one embodiment in various places in the specification do not necessarily all refer to the same embodiment.

What is claimed is:

1. A method comprising:
    capturing video of an eye exposed to light stimuli over a predetermined time using a video camera of a portable video capture device (PVCD);
    processing the video to locate at least one feature of the eye;
    measuring a change in the feature over the predetermined time in response to the light stimuli;
    analyzing data from the measured change in the feature, wherein analyzing data includes extracting data from the measured change in the feature, calculating a number of parameters from the extracted data, correlating the calculated parameters against predetermined reference parameters and predicting a degree of cognitive impairment based on the results of the correlation; and
    outputting through a user interface in the portable video capture device the degree of impairment to a user.

2. The method of claim 1, further comprising prior to processing the video collecting environmental data including ambient light, PVCD orientation and movement from sensors in the PVCD, and calibrating the measured change in the feature based on the environmental data.

3. The method of claim 1, wherein processing the video to locate a feature of the eye comprises locating a pupil and an iris of the eye.

4. The method of claim 3, wherein measuring the change in the feature over the predetermined time comprises measuring the size of the pupil relative to the iris in a first frame of video captured at a first time and comparing the size measured in the first frame to a size measured in the same way in a second frame video captured at a later time relative to the first frame, and continuing to subsequent frames.

5. The method of claim 3, wherein processing the video further comprises authenticating an identity of the user by applying an iris recognition algorithm to the captured video of the eye.

6. The method of claim 5, further comprising transmitting the identity of the user and the degree of impairment to a remote server and retrieve a responding message.

7. The method of claim 3, wherein calculating a number of parameters from the extracted data comprises calculating parameters of pupillary constriction after exposure to the light stimuli, parameters of pupillary re-dilation after constriction, or both.

8. The method of claim 1, wherein calculating a number of parameters from the extracted data comprises of detecting and calculating parameters of involuntary eye movements.

9. The method of claim 1, further comprising prior to analyzing data from the measured change in the feature, receiving from the user quantitative values of physical traits, including one or more of age, gender, height, weight, ethnicity and body mass.

10. The method of claim 9, wherein the predetermined reference parameters include normative parameters derived from measurements of a number of non-cognitive impaired individuals sharing similar physical traits with the user.

11. The method of claim 1, wherein the predetermined reference parameters include normative parameters derived from one or more measurements of the user previously collected while the user was in a non-cognitive impaired state.

12. The method of claim 1, further comprising, if the degree of impairment exceeds predetermined values, of providing to the user contact information for a number of commercial transportation services, emergency services or individuals previously specified by the user.

13. The method of claim 12, further comprising of automatically contacting one of the predetermined individuals or services previously specified by the user.

14. A method comprising:
    running on a portable video capture device (PVCD) a smart user interface (SUI) software comprising of code to determine the position of the PVCD and instructions to guide a user to position the PVCD for optimal video capture of an eye of the user with a camera of the PVCD;
    self-capturing video of the eye over a predetermined time, wherein the self-captured video includes video of the eye before, during and following exposure of the eye to light stimuli from a light source of the PVCD;
    processing the video to locate a feature of the eye;
    measuring a change in the feature over the predetermined time in response to the light stimuli;
    analyzing data from the measured change in the feature, and predicting a degree of cognitive impairment based on the measured change; and
    outputting through an interface in the portable video capture device the degree of cognitive impairment to the user.

15. The method of claim 14, further comprising prior to processing the video, collecting environmental data including PVCD orientation and movement from sensors in the PVCD to guide user to position PCVD for video capture.

16. The method of claim 14, further comprising prior to processing the video collecting environmental data including ambient light, PVCD orientation and movement from sensors in the PVCD, and calibrating the measured change in the feature based on the environmental data.

17. The method of claim 14, wherein processing the video to locate a feature of the eye comprises locating a pupil and an iris of the eye.

18. The method of claim 17, wherein measuring the change in the feature over the predetermined time comprises measuring the size of the pupil relative to the iris in a first frame of video captured at a first time and comparing the size measured in the first frame to a size measured in the same way in a second frame video captured at a later time relative to the first frame, and continuing to subsequent frames.

19. The method of claim 17, wherein processing the video further comprises authenticating an identity of the user by applying an iris recognition algorithm to the captured video of the eye.

20. The method of claim 19, further comprising transmitting the identity of the user and the degree of impairment to a remote server and retrieve a responding message.

21. The method of claim 14, wherein a size of the eye within the framing mask guides the user to adjust a distance between the eye and the PVCD.

22. The method of claim 14, wherein a size of the eye within a video frame is measured in real time and audio/video feedback is provided to guide the user to adjust a distance between the eye and the PVCD.

23. The method of claim 14, wherein real time data from PVCD environment sensors and camera parameters is used to guide user to adjust distance, tilt and rotation of PVCD relative to the eye.

24. The method of claim 14, wherein a removable add-on positioning device attached to a PVCD is used to station the PVCD in the optimal position for video capture.

25. A system comprising:
   a portable video capture device (PVCD) including a user interface, a video capture device, a light source, and a local processor; and
   a software program and executed by the local processor, the software program including:
      a video capture module to capture video of an eye exposed to light stimuli from the light source over a predetermined time using the video capture device of the PVCD;
      local correlation and prediction module to: locate a feature of the eye; measure a change in the feature over the predetermined time in response to a light stimuli from the light source; extract data from the measured change in the feature; calculate a number of parameters from the extracted data; correlate the calculated parameters with predetermined reference parameters and predict a degree of impairment based on the results of the correlation; and
      a user interface module to output the probability and degree of impairment to a user.

26. The system of claim 25, wherein the PVCD further comprises sensors for collecting environmental data including ambient light, PVCD orientation and movement in the PVCD, and wherein the local correlation and prediction module further comprises computer program code to calibrate the measured change in the feature based on the environmental data.

27. The system of claim 25, wherein the feature of the eye comprises an iris, and wherein the
   local correlation and prediction module further comprises computer program code to authenticate an identity of the user by applying an iris recognition algorithm to the captured video of the eye.

28. The system of claim 27, wherein the software program further comprises computer program code to transmit the identity of the user and a probability and degree of impairment to a remote server and retrieve a responding message.

29. The system of claim 25, includes a network interface device through which the PVCD is coupled to remote memory and the software program may be at least partially stored in the remote memory.

* * * * *